United States Patent [19]

Sommer et al.

[11] Patent Number: 4,677,222

[45] Date of Patent: Jun. 30, 1987

[54] KETOBENZYLCARBAMATES

[75] Inventors: Harold Z. Sommer, Havre de Grace; George E. Wicks, Jr., Baltimore; Omer O. Owens, Abingdon, all of Md.

[73] Assignee: The United States of America as represented by the Secretary of the Army, Washington, D.C.

[21] Appl. No.: 699,744

[22] Filed: Jan. 22, 1968

[51] Int. Cl.[4] .............................................. C07C 125/04

[52] U.S. Cl. ...................................... 560/133; 514/483

[58] Field of Search .................... 260/482 B; 424/300; 560/133; 514/483

[56] References Cited

U.S. PATENT DOCUMENTS

| | | | |
|---|---|---|---|
| 3,188,955 | 6/1965 | Brown | 102/24 |
| 4,241,211 | 12/1980 | Sommer et al. | 546/261 |
| 4,246,415 | 1/1981 | Sommer et al. | 546/261 |
| 4,246,416 | 1/1981 | Sommer et al. | 546/261 |

*Primary Examiner*—John F. Terapane
*Assistant Examiner*—Eric Jorgensen
*Attorney, Agent, or Firm*—Anthony T. Lane; Robert P. Gibson; Harold H. Card, Jr.

[57] ABSTRACT

New chemical compounds, bis-quaternary carbamates, having the generic formula:

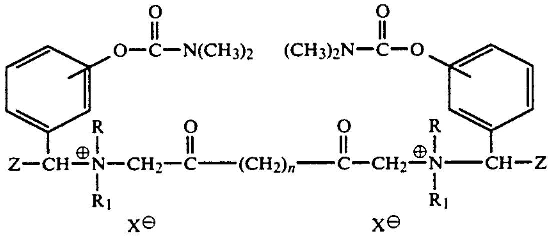

wherein X is one equivalent of a monovalent or polyvalent anion, wherein R and $R_1$ are aliphatic radicals selected from the group consisting of methyl, ethyl, propyl, isopropyl, butyl, isobutyl, pentyl, hexyl, wherein Z is a radical selected from the group consisting of hydrogen, methyl, or ethyl, wherein n is 2-12, wherein the dimethylcarbamoxy group is in the ortho, meta, or para position in the benzyl moiety, and having utility as toxic agents.

2 Claims, No Drawings

KETOBENZYLCARBAMATES

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quaternary compounds, the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields, said agents being well suited for industrial scale manufacture.

Othe objects of and uses for the invention will in part be obvious and will in part appear hereinafter in the following detailed description thereof.

Our compounds may be employed in any munition suitable for handling a relatively non-volatile toxic agent such as bombs, shells, spray tanks, rockets, missiles, aerosol generators, and others.

In accordance with our invention a carbamylated benzyldialkylamine was quarternized with a ketodihalide in a solvent such as acetonitrile or acetone either under reflux conditions or by allowing the reaction mixture to stand at room temperature for prolonged periods of time. After the reaction took place, an oily material precipitated, or the addition of a solvent such as ethyl acetate, acetone, or ether caused an oil to separate, depending on the particular amine starting material. The supernatant solvent mixture was decanted and the remaining oil was stirred in a solvent such as acetone. In some cases the oily material solidified, in others it became very viscous and gumlike depending on the particular amine starting material. The crude product, thus obtained, was purified by dissolving it in a solvent, such as acetonitrile, treating the solution with decolorizing charcoal, precipitating the pure product by addition of a solvent, such as ethyl acetate, and drying the product. The resultant white crystalline material constitutes the new compounds of our invention which may be represented by the following generic formula:

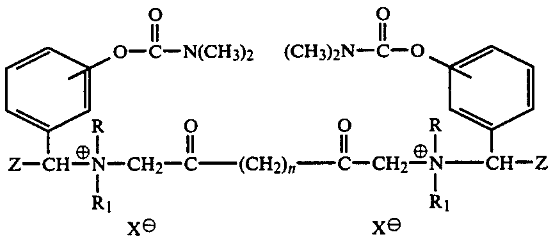

wherein X is one equivalent of a monovalent or polyvalent anion, wherein R and $R_1$ are aliphatic radicals selected from the group consisting of methyl, ethyl, propyl, isopropyl, butyl, isobutyl, pentyl, or hexyl, wherein Z is a radical selected from the group consisting of hydrogen, methyl, or ethyl, wherein n is 2–12, and wherein the dimethylcarbamoxy group is in the ortho, meta, or para position in the benzyl moiety.

The procedure used for the preparation of the new toxic materials is schematically shown below:

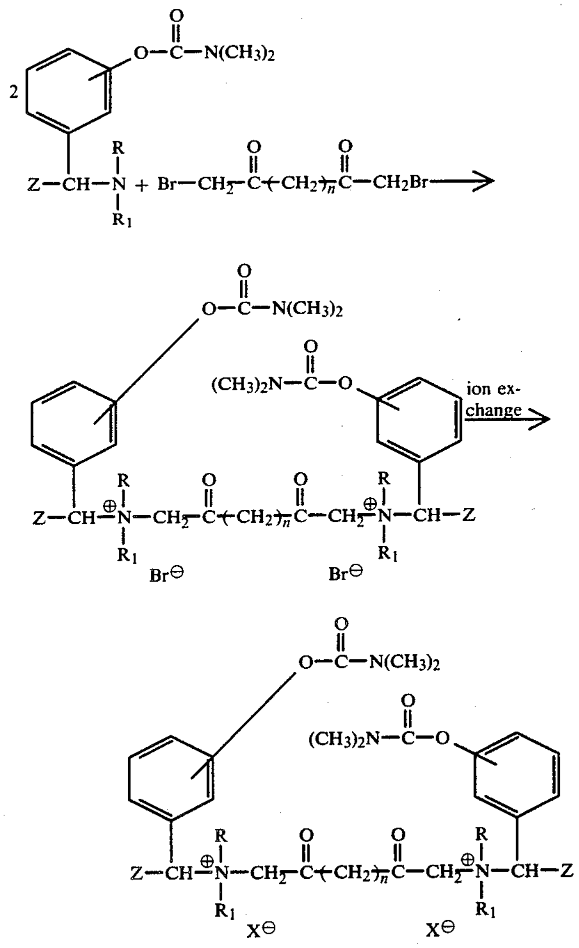

wherein X is a halide ion, preferably bromide, and R, $R_1$, Z, n, and the position of the dimethylcarbamoxy group as defined above.

If compounds are desired in which X is other than a halide ion, the above quaternary compounds are treated with the desired acid by simple exchange reactions as set forth below.

EXAMPLE 1

2-Dimethylcarbamoxybenzyldimethylamine (1.8 g) and 1,10-dibromodecane-2,9-dione (1.3 g) were dissolved in 10 ml of acetonitrile and the solution was allowed to stand at room temperature overnight. The addition of about 50 ml of ethyl acetate caused an oily material to separate. The supernatant solvent mixture was decanted and, upon stirring the residue in about 50 ml of boiling acetone, it solidified. The solid was collected on a filter and purified by dissolving it in acetonitrile, treating the solution with decolorizing charcoal, and precipitating the product by addition of ethyl acetate. After filtration and drying, 2.6 g of 1,10-bis[N-(2-dimethylcarbamoxybenzyl)-N,N-dimethylammonio]-decane-2,9-dione dibromide was obtained as a white crystalline material, m.p. 189°-191° C.

Analysis for $C_{34}H_{52}Br_2N_4O_6$. Calcd: C, 52.9; H, 6.8; Br, 20.7. Found: C, 52.6; H, 6.9; Br, 20.4.

| Toxicity IV $LD_{50}$ | |
|---|---|
| Rabbits | Mice |
| 0.005 mg/kg | 0.014 mg/kg |

EXAMPLE 2

2-(1-Dimethylaminoethyl)dimethylcarbamoxybenzene (0.95 g) and 1,10-dibromodecane-2,9-dione (0.65 g) were dissolved in 10 ml of acetone and the solution refluxed for about 4 hours, during which time an oily material separated. The supernatant solvent was decanted and the remaining oil dissolved in about 20 ml of acetonitrile. This solution was treated with decolorizing carbon, and, upon addition of about 60 ml of ethyl acetate to the purified solution, a viscous gumlike material precipitated. The solvent mixture was decanted and the residue dried under reduced pressure (0.5 mm) at room temperature for about 16 hours. During the drying, the product changed its consistency to a white hygroscopic solid. Thus, 0.95 g of 1,10-bis{N-[1-(2-dimethylcarbamoxyphenyl)ethyl]-N,N-dimethylammonio}decane-2,9-dione dibromide was obtained. Due to the hygroscopicity of the compound, a sample was converted to and analyzed as the tetraphenylboronate salt. The above dibromide salt was dissolved in water and to this solution an aqueous solution of sodium tetraphenylboron (in molar excess) was added. The solid precipitate that formed was collected on a filter, washed several times with water and dried. The tetraphenylboronate salt melted at 82°-84° C.

Analysis for $C_{84}H_{96}B_2N_4O_6$. Calcd: C, 78.9; H, 7.6; N, 4.4. Found: C, 78.8; H, 7.7; N, 4.5.

| Toxicity IV $LD_{50}$ | |
|---|---|
| Rabbits | Mice |
| 0.006 mg/kg | 0.018 mg/kg |

EXAMPLE 3

2-Dimethylcarbamoxybenzyldimethylamine (1.8 g) and 1,8-dibromooctane-2,7-dione (1.2 g) were dissolved in 25 ml of acetone and the reaction mixture was allowed to stand for about 2 days at room temperature, during which time a viscous oil separated. The supernatant solvent was decanted and about 50 ml of acetone was added to the remaining oil. After stirring the mixture for about 15 minutes and allowing it to stand at room temperature overnight, the oil solidified. The solid was collected on a filter and purified by dissolving it in acetonitrile (about 25 ml), treating the solution with decolorizing carbon, and precipitating the product with ethyl acetate (about 60 ml). After drying, 0.55 g of white crystalline 1,8-bis[N-(2-dimethylcarbamoxybenzyl)-N,N-dimethylammonio]octane-2,7-dione dibromide was obtained having a m.p. 165°-169° C.

Analysis for $C_{32}H_{48}Br_2N_4O_6 \cdot \frac{1}{2}H_2O$. Calcd: C, 51.1; H, 6.6; Br, 21.2; O, 13.8. Found: C, 51.1; H, 6.8; Br, 20.9; O, 13.8.

| Toxicity IV $LD_{50}$ | |
|---|---|
| Rabbits | Mice |
| 0.005 mg/kg | 0.056 mg/kg |

The compounds that are representative of our invention are listed below by name and chemical structure.

1,6-bis[N-(2-dimethylcarbamoxybenzyl)-N,N-dimethylammonio]hexane-2,5-dione dibromide.

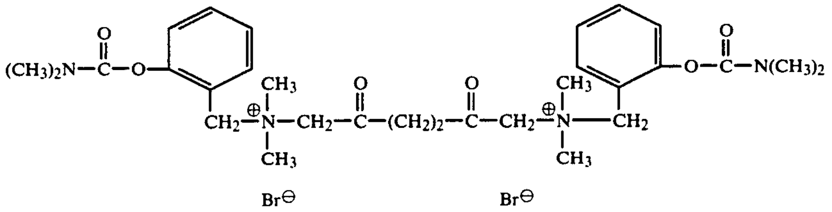

1,7-bis[N-(2-dimethylcarbamoxybenzyl)-N,N-dimethylammonio]heptane-2,6-dione dibromide.

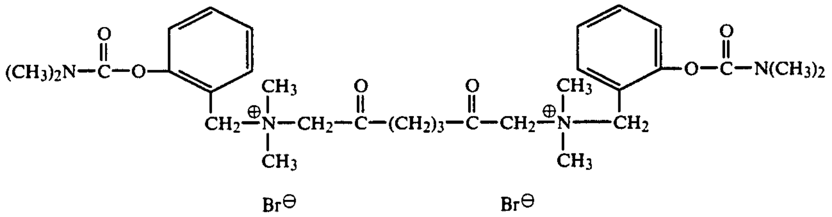

1,8-bis[N-(2-dimethylcarbamoxybenzyl)-N,N-dimethylammonio]octane-2,7-dione dibromide.

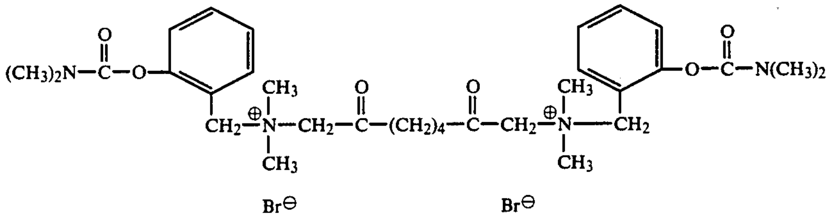

1,9-bis[N-(2-dimethylcarbamoxybenzyl)-N,N-dimethylammonio]nonane-2,8-dione dibromide.

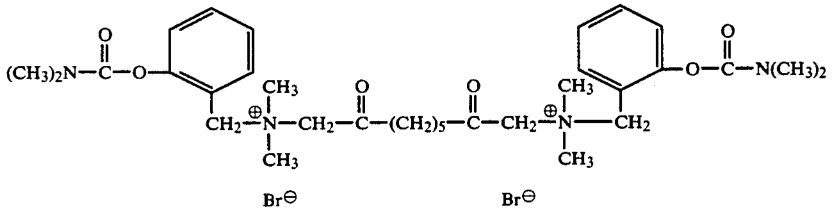

1,10-bis[N-(2-dimethylcarbamoxybenzyl)-N,N-dimethylammonio]decane-2,9-dione dibromide.

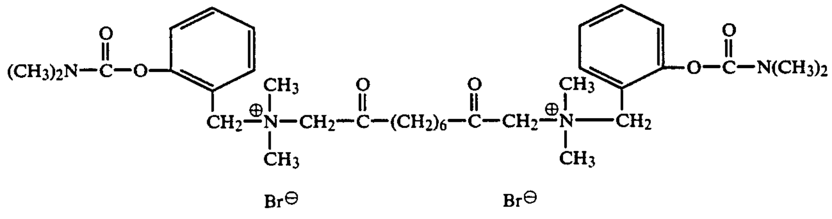

1,12-bis[N-(2-dimethylcarbamoxybenzyl)-N,N-dimethylammonio]dodecane-2,11-dione dibromide.

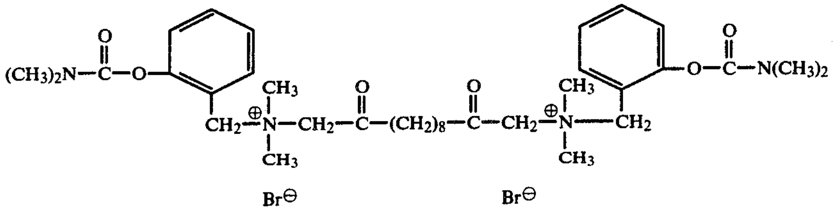

1,16-bis[N-(2-dimethylcarbamoxybenzyl)-N,N-dimethylammonio]hexadecane-2,15-dione dibromide.

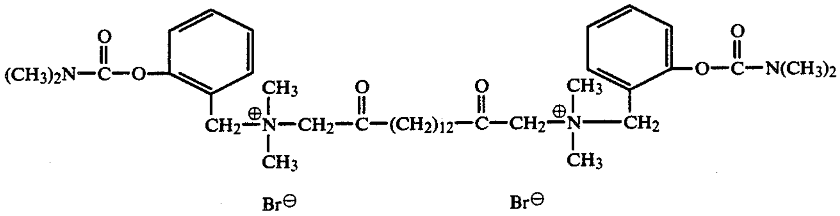

1,10-bis{N-[1-(2-dimethylcarbamoxyphenyl)ethyl]-N,N-dimethylammonio}decane-2,9-dione dibromide.

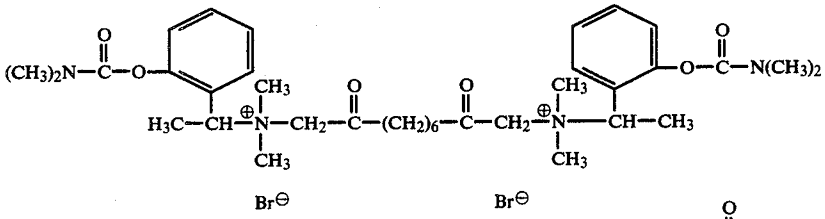

1,10-bis[N-(3-dimethylcarbamoxybenzyl)-N,N-dimethylammonio]decane-2,9-dione dibromide.

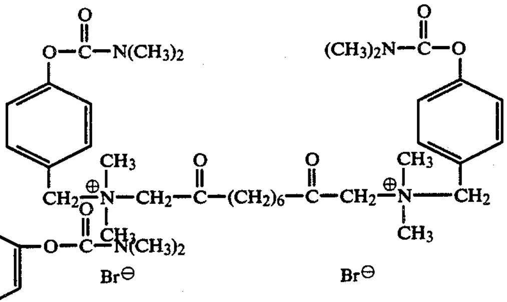

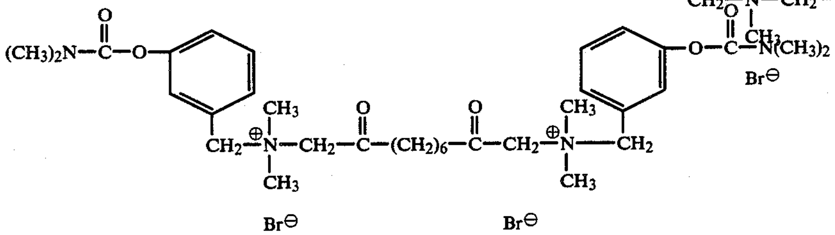

1,10-bis[N-(4-dimethylcarbamoxybenzyl)-N,N-dimethylammonio]decane-2,9-dione dibromide.

1,10-bis[N-(2-dimethylcarbamoxybenzyl)-N-ethyl-N-methylammonio]decane-2,9-dione dibromide.

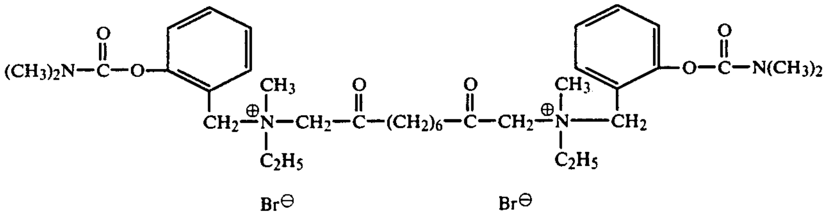

1,10-bis[N-(2-dimethylcarbamoxybenzyl)-N,N-diethylammonio]decane-2,9-dione dibromide.

1,10-bis[N-(2-dimethylcarbamoxybenzyl)-N-isopropyl-N-methylammonio]decane-2,9-dione dibromide.

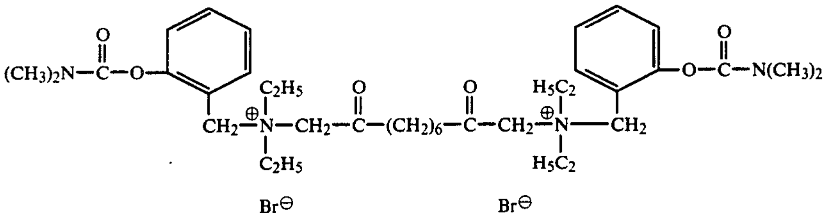

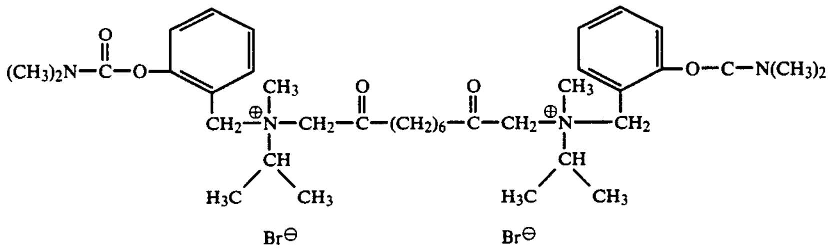

1,10-bis[N-(2-dimethylcarbamoxybenzyl)-N-methyl-N-propylammonio]decane-2,9-dione dibromide.

1,10-bis[N-(2-dimethylcarbamoxybenzyl)-N-butyl-N-methylammonio]decane-2,9-dione dibromide.

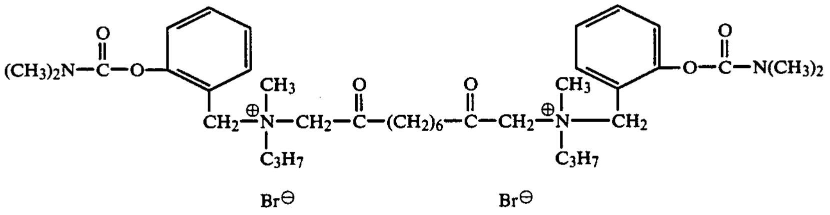

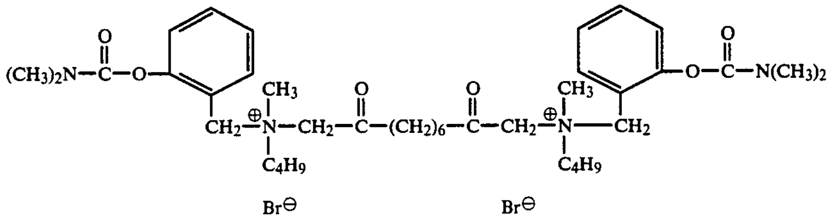

1,10-bis[N-(2-dimethylcarbamoxybenzyl)-N-isobutyl-N-methylammonio]decane-2,9-dione dibromide.

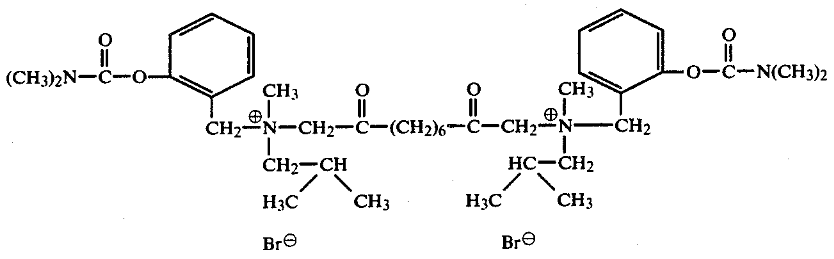

1,10-bis[N-(2-dimethylcarbamoxybenzyl)-N-methyl-N-pentylammonio]decane-2,9-dione dibromide.

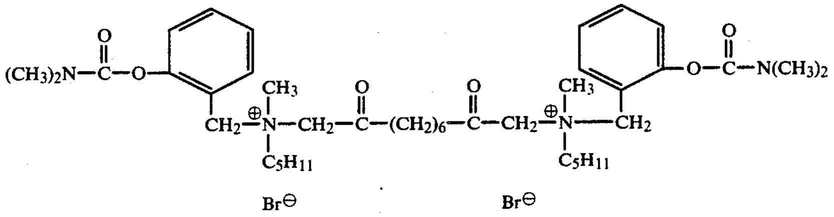

1,10-bis[N-(2-dimethylcarbamoxybenzyl)-N-hexyl-N-methylammonio]decane-2,9-dione dibromide.

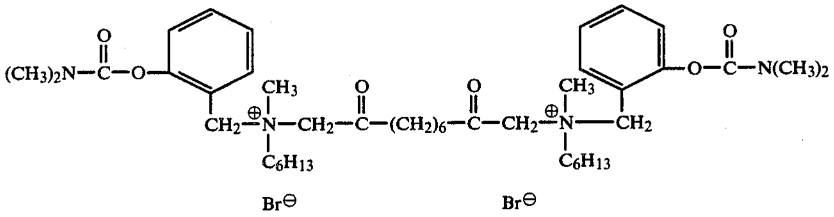

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus, the halogen ions can be exchanged with other anions of relatively strong monovalent or polyvalent acid by conventional methods. For example, if X— is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, nitrate, tetraphenylboronate, and hydrogen sulfate. Representative examples of these additional end products are:

1,10-bis[N-(2-dimethylcarbamoxybenzyl)-N,N-dimethylammonio]decane-2,9-dione di(hydrogen oxalate);

1,10-bis[N-(2-dimethylcarbamoxybenzyl)-N,N-dimethylammonio]decane-2,9-dione diperchlorate;

1,10-bis[N-(2-dimethylcarbamoxybenzyl)-N,N-dimethylammonio]decane-2,9-dione dinitrate;

1,10-bis[N-(2-dimethylcarbamoxybenzyl)-N,N-dimethylammonio]decane-2,9-dione di(tetraphenylboronate);

1,10-bis[N-(2-dimethylcarbamoxybenzyl)-N,N-dimethylammonio]decane-2,9-dione di(hydrogen sulfate).

We claim:

1. Chemical compounds having the generic formula:

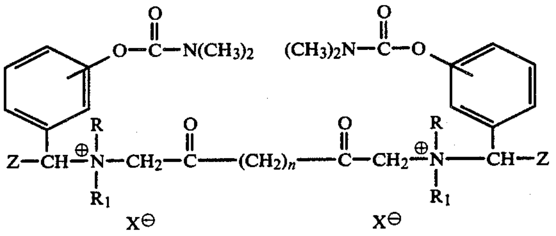

wherein X is one equivalent of an anion selected from monovalent and polyvalent anions, said anions being selected from the group consisting of halide, hydrogen oxalate, perchlorate, hydrogen sulfate, nitrate, and tetraphenylboronate; wherein R and $R_1$ are aliphatic radicals selected from the group consisting of methyl, ethyl, propyl, isopropyl, butyl, isobutyl, pentyl, and hexyl; wherein Z is a radical selected from the group consisting of hydrogen, methyl, and ethyl; wherein n is selected from 2–12; and wherein the dimethylcarbamoxy group is in the position selected from ortho, meta, and para in the benzyl moiety.

2. Chemical compounds selected from the group of compounds having the names:

1,8-bis[N-(2-dimethylcarbamoxybenzyl)-N,N-dimethylammonio]octane-2,7-dione dibromide;

1,10-bis[N-(2-dimethylcarbamoxybenzyl)-N,N-dimethylammonio]decane-2,9-dione dibromide;

1,10-bis{N-[1-(2-dimethylcarbamoxyphenyl)ethyl]-N,N-dimethylammonio}decane-2,9-dione dibromide;

1,10-bis[N-(2-dimethylcarbamoxybenzyl)-N,N-diethylammonio]decane-2,9-dione dibromide;

1,10-bis[N-(2-dimethylcarbamoxybenzyl)-N-methyl-N-propylammonio]decane-2,9-dione dibromide;

1,10-bis[N-(2-dimethylcarbamoxybenzyl)-N-isopropyl-N-methylammonio]decane-2,9-dione dibromide;

1,10-bis[N-(2-dimethylcarbamoxybenzyl)-N-butyl-N-methylammonio]decane-2,9-dione dibromide.

* * * * *